US011462027B2

(12) United States Patent
Sano et al.

(10) Patent No.: US 11,462,027 B2
(45) Date of Patent: Oct. 4, 2022

(54) EYE OPENING DEGREE CALCULATION DEVICE

(71) Applicant: TOYOTA JIDOSHA KABUSHIKI KAISHA, Toyota (JP)

(72) Inventors: Masataka Sano, Tokyo-to (JP); Yosuke Morino, Tokyo-to (JP); Kimimasa Tamura, Tokyo-to (JP); Koichiro Yamauchi, Tokyo-to (JP); Takuya Sakata, Tokyo-to (JP); Taku Mitsumori, Tokyo-to (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 0 days.

(21) Appl. No.: 17/207,828

(22) Filed: Mar. 22, 2021

(65) Prior Publication Data

US 2021/0303889 A1 Sep. 30, 2021

(30) Foreign Application Priority Data

Mar. 24, 2020 (JP) .............................. JP2020-053052

(51) Int. Cl.
*G06V 20/59* (2022.01)
*A61B 3/113* (2006.01)
*B60W 40/08* (2012.01)

(52) U.S. Cl.
CPC ............ *G06V 20/597* (2022.01); *A61B 3/113* (2013.01); *B60W 40/08* (2013.01); *B60W 2040/0827* (2013.01); *B60W 2040/0872* (2013.01)

(58) Field of Classification Search
None
See application file for complete search history.

(56) References Cited

U.S. PATENT DOCUMENTS

| 9,775,512 B1* | 10/2017 | Tyler ..................... G06V 20/64 |
| 10,331,942 B2* | 6/2019 | Wong ..................... G06V 40/45 |
| 2008/0069551 A1* | 3/2008 | Wakamatsu ........... G03B 17/00 396/55 |
| 2009/0268022 A1* | 10/2009 | Omi ........................ A61B 5/18 348/135 |

(Continued)

FOREIGN PATENT DOCUMENTS

| JP | 2010134608 A | * | 6/2010 |
| JP | 2010134608 A |   | 6/2010 |

(Continued)

*Primary Examiner* — Muhammad Adnan
(74) *Attorney, Agent, or Firm* — Dickinson Wright, PLLC

(57) ABSTRACT

An eye opening degree calculation device includes: a processor configured to: calculate a degree of eye opening of a crew, based on an image in which a face of the crew appears; calculate a face direction angle of the crew with respect to a predetermined reference direction, based on the image; calculate a line-of-sight angle of the crew with respect to the predetermined reference direction, based on the image; correct the degree of eye opening or a threshold value which will be compared with the degree of eye opening, when a difference between the face direction angle and the line-of-sight angle is equal to or greater than a predetermined value; and determine an eye opening state of the crew, based on the corrected degree of eye opening or a comparison result of the degree of eye opening with the corrected threshold value.

6 Claims, 4 Drawing Sheets

(56) References Cited

U.S. PATENT DOCUMENTS

| | | | | |
|---|---|---|---|---|
| 2011/0216181 A1* | 9/2011 | Yoda | ................. | A61B 5/18 |
| | | | | 348/78 |
| 2013/0142389 A1* | 6/2013 | Shimura | ............. | G06V 40/197 |
| | | | | 382/103 |
| 2014/0147019 A1* | 5/2014 | Hanita | .................. | G06T 7/11 |
| | | | | 382/117 |
| 2014/0176901 A1* | 6/2014 | Espinola Estepa | .... | G02C 7/022 |
| | | | | 351/159.01 |
| 2016/0086304 A1* | 3/2016 | Hsieh | ................. | G06V 40/171 |
| | | | | 382/201 |
| 2016/0262682 A1* | 9/2016 | Omi | ................. | A61B 5/7455 |
| 2018/0285628 A1* | 10/2018 | Son | .................. | G06K 9/6215 |
| 2019/0147268 A1* | 5/2019 | Hayashi | ............... | G06V 40/193 |
| | | | | 382/103 |
| 2021/0070306 A1* | 3/2021 | Yamauchi | ............ | G06V 20/597 |
| 2021/0197835 A1* | 7/2021 | Maeda | ................ | B60W 40/09 |

FOREIGN PATENT DOCUMENTS

| | | | |
|---|---|---|---|
| JP | 2013120442 A | | 6/2013 |
| JP | 2019012429 A | | 1/2019 |
| JP | 2019087170 A | | 6/2019 |

\* cited by examiner

EYE OPENING DEGREE CALCULATION DEVICE

FIELD OF THE INVENTION

The present invention relates to an eye opening degree calculation device.

BACKGROUND OF THE INVENTION

In relation to an eye open-close detection device, for example, there is a technology of calculating an amount of eye opening from a facial image of a driver and calculating a degree of eye opening according to a comparison result with a reference eye opening amount distribution being a reference of an amount of eye opening, as described in Japanese Unexamined Patent Publication (Kokai) No. 2013-120442.

SUMMARY OF THE INVENTION

A face direction angle and a line-of-sight angle of a driver do not necessarily match, and a degree of eye opening may be erroneously calculated when the difference between the face direction angle and the line-of-sight angle increases. When the driver's degree of arousal is determined based on the degree of eye opening in such a case, the degree of eye opening is different from the actual value, and therefore the degree of arousal may be erroneously determined.

Then, an object of the present invention is to provide an eye opening degree calculation device capable of accurately determining an eye opening state even when the angular difference between a face direction angle and a line-of-sight angle is large.

The present invention was made so as to solve the above problem and has as its gist the following.

(1) An eye opening degree calculation device comprising:
a processor configured to:
calculate a degree of eye opening of a crew, based on an image in which a face of the crew appears;
calculate a face direction angle of the crew with respect to a predetermined reference direction, based on the image;
calculate a line-of-sight angle of the crew with respect to the predetermined reference direction, based on the image;
correct the degree of eye opening or a threshold value which will be compared with the degree of eye opening, when a difference between the face direction angle and the line-of-sight angle is equal to or greater than a predetermined value; and
determine an eye opening state of the crew, based on the corrected degree of eye opening or a comparison result of the degree of eye opening with the corrected threshold value.

(2) The eye opening degree calculation device according to above (1), wherein the processor corrects the degree of eye opening to a value corresponding to a case of the face direction angle and the line-of-sight angle pointing forward, based on the difference.

(3) The eye opening degree calculation device according to above (1), wherein the processor corrects the degree of eye opening in such a way as to increase the degree of eye opening when the line-of-sight angle points more downward than the face direction angle and corrects the degree of eye opening in such a way as to decrease the degree of eye opening when the line-of-sight angle points more upward than the face direction angle.

(4) The eye opening degree calculation device according to above (3), wherein the processor increases an amount of correction of the degree of eye opening as the difference increases.

(5) The eye opening degree calculation device according to above (1), wherein the processor corrects the threshold value in such a way as to decrease the threshold value when the line-of-sight angle points more downward than the face direction angle and corrects the threshold value in such a way as to increase the threshold value when the line-of-sight angle points more upward than the face direction angle.

(6) The eye opening degree calculation device according to above (5), wherein the processor increases an amount of correction of the threshold value as the difference increases.

The eye opening degree calculation device according to the present invention provides an effect of capability of accurately determining an eye opening state even when the angular difference between a face direction angle and a line-of-sight angle is large.

DESCRIPTION OF EMBODIMENTS

Referring to drawings, an eye opening degree calculation device will be described below. For example, the eye opening degree calculation device calculates a degree of eye opening of a crew of a vehicle and corrects the calculated degree of eye opening when the difference between a face direction angle and a line-of-sight angle of the crew with respect to a predetermined reference direction is equal to or greater than a predetermined value. Further, the eye opening degree calculation device corrects a threshold value which will be compared with the degree of eye opening when the difference between the face direction angle and the line-of-sight angle of the crew with respect to the predetermined reference direction is equal to or greater than the predetermined value.

By the degree of eye opening or the threshold value which will be compared with the degree of eye opening being corrected when the difference between the face direction angle and the line-of-sight angle is equal to or greater than the predetermined value, erroneous determination of an eye opening state caused by the face direction angle being different from the line-of-sight angle is securely suppressed.

Figure 1:
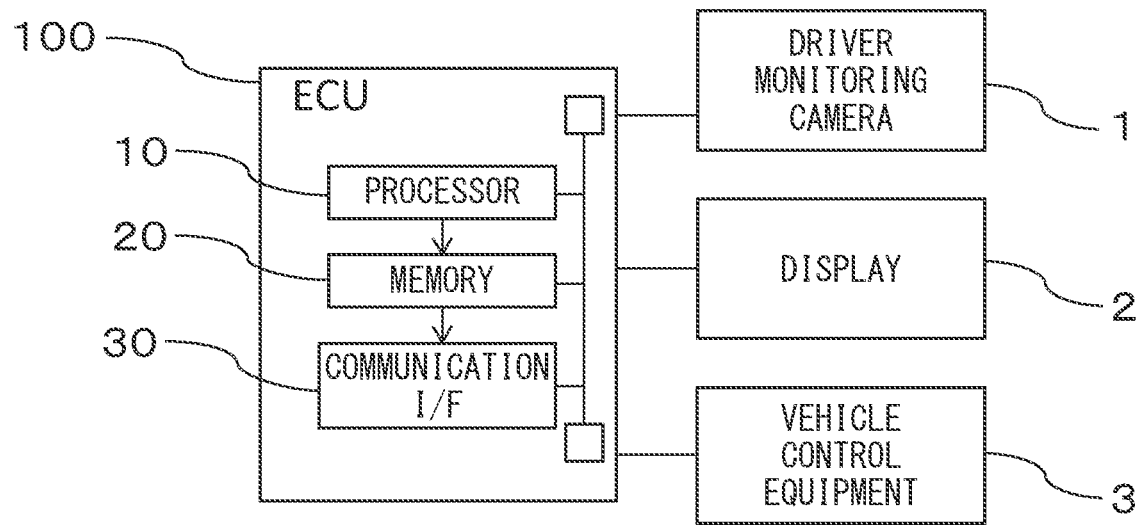
FIG. 1 is a schematic configuration diagram of an eye opening degree calculation system on which an eye opening degree calculation device is installed according to one embodiment.

FIG. 1 is a schematic configuration diagram of a vehicle control system 200 on which an eye opening degree calculation device is installed according to one embodiment. For example, the vehicle control system 200 is equipped on a vehicle and determines an eye opening state of a crew such as a driver. Note that a case of the crew being a driver will be described as an example in the following description. The vehicle control system 200 includes a driver monitoring camera 1 capturing an image of the driver's face and generating a facial image, a display 2 displaying a warning to the driver, and the like, vehicle control equipment 3 controlling the vehicle, and a control device (ECU) 100 determining an eye opening state of the driver's eye. The driver monitoring camera 1, the display 2, the vehicle control equipment 3, and the control device 100 are communicably connected to one another through an on-board network conforming to a standard such as a controller area network (CAN).

The driver monitoring camera 1 includes a two-dimensional detector configured with an array of photoelectric conversion elements sensitive to visible light, such as a CCD or a C-MOS, and an image formation optical system forming, on the two-dimensional detector, an image of a region being an image capture target. The driver monitoring camera 1 is provided in the neighborhood of a dashboard, a windshield, or the like inside the vehicle, is directed to an assumed position of the driver, and captures an image of the driver's face. The driver monitoring camera 1 captures an image of the driver's face on a predetermined capture cycle (such as 1/30 to 1/10 seconds) and generates an image in which the driver's face appears. It is preferable that an image acquired by the driver monitoring camera 1 be a color image. Every time the driver monitoring camera 1 generates an image, the driver monitoring camera 1 outputs the generated image to the control device 100 through the on-board network. Further, the driver camera 1 includes a near infrared light source irradiating the driver's eye with near infrared rays.

For example, the display 2 is configured with a liquid crystal display (LCD), is provided in the neighborhood of a meter panel, a dashboard, or the like, and displays a warning to the driver as needed. The vehicle control equipment 3 includes a steering device steering the vehicle, a braking device braking the vehicle, and the like.

The control device 100 is a component controlling the entire vehicle control system 200 and is an embodiment of an eye opening degree calculation device. The control device 100 includes a processor 10, a memory 20, and a communication interface 30. The processor 10 includes one or a plurality of central processing units (CPUs) and peripheral circuits thereof. The processor 10 may further include another arithmetic circuit such as an arithmetic logic unit, a numeric processing unit, or a graphical processing unit. For example, the memory 20 includes a volatile semiconductor memory and a nonvolatile semiconductor memory and stores data related to processing according to the present embodiment as needed. The communication interface 30 is an example of a communication unit and includes an interface circuit for connecting the control device 100 to the on-board network.

Figure 2:
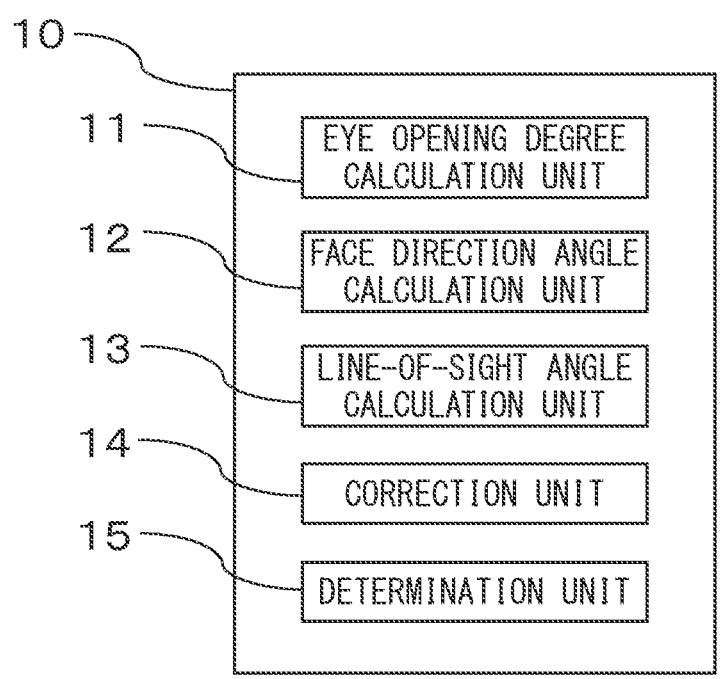
FIG. 2 is a schematic diagram illustrating functional blocks of a processor on a control device.

FIG. 2 is a schematic diagram illustrating functional blocks of the processor 10 in the control device 100. The processor 10 in the control device 100 includes an eye opening degree calculation unit 11, a face direction angle calculation unit 12, a line-of-sight angle calculation unit 13, a correction unit 14, and a determination unit 15. For example, each unit included in the processor 10 is a functional module provided by a computer program operating on the processor 10. In other words, a functional block of the processor 10 is configured with the processor 10 and a program (software) for causing the processor 10 to function. Further, the program may be recorded in the memory 20 included in the control device 100 or an externally connected recording medium. Alternatively, each unit included in the processor 10 may be a dedicated arithmetic circuit provided in the processor 10.

In the vehicle control system 200 configured as described above, the eye opening degree calculation unit 11 in the processor 10 calculates the driver's degree of eye opening, based on an image in which the driver's face appears, the image being generated by the driver monitoring camera 1. Further, the face direction angle calculation unit 12 in the processor 10 calculates the driver's face direction angle with respect to a predetermined reference direction. Further, the line-of-sight angle calculation unit 13 in the processor 10 calculates the driver's line-of-sight angle with respect to the predetermined reference direction. An angle according to the present embodiment refers to an angle in a vertical direction, that is, an angle in a direction in which a human face nods.

By using a known technique, the eye opening degree calculation unit 11 first detects the driver's eye from an image generated by the driver monitoring camera 1 and determines a contour of the eye. Examples of a technique of detecting a contour of an eye from an image include a technique of optimizing (fitting) model parameters in such a way as to minimize the distance between a feature point of a face model (PDM) modeled by three-dimensional coordinate data and a feature point extracted from a facial image by a feature point extractor, the technique being described in a literature (Hiroyuki Takano and Koichiro Deguchi, "Use of facial contours for handling postural changes in face alignment by contours," Information Processing Society of Japan Technical Report, Sep. 2, 2012). For example, by using the technique, the eye opening degree calculation unit 11 determines a three-dimensional position of a contour of an eye, based on optimized model parameters. Further, in addition to a three-dimensional position of an eye, three-dimensional positions of parts of a face such as a nose and a mouth are determined by the technique.

When determining the three-dimensional position of the contour of the eye, the eye opening degree calculation unit 11 detects a degree of eye opening from the distance between the upper eyelid and the lower eyelid. The eye opening degree calculation unit 11 detects the degree of eye opening by using a table or a function defining a relation between a distance between the upper eyelid and the lower eyelid, and a degree of eye opening, the table or the function being previously stored in the memory 20, and applying the distance between the upper eyelid and the lower eyelid to the table or the function. Alternatively, the eye opening degree calculation unit 11 may use a table or a function defining a relation between an aspect ratio of the eye and a degree of eye opening and determine the degree of eye opening from the aspect ratio of the eye. Further, the eye opening degree calculation unit 11 may calculate the distance between the upper eyelid and the lower eyelid itself or the aspect ratio of the eye itself as a degree of eye opening.

The face direction angle calculation unit 12 in the processor 10 calculates the driver's face direction angle with respect to a predetermined reference direction, based on an image. For example, the face direction angle calculation unit 12 calculates a face direction angle (pitch angle), based on the distance between the nose position and a straight line connecting the positions of the left and right eyes, by use of a technique described in Japanese Unexamined Patent Publication (Kokai) No. 2015-75915 or the like.

The line-of-sight angle calculation unit 13 in the processor 10 calculates a line-of-sight angle with respect to the predetermined reference direction, based on an image, by a known line-of-sight detection method. Examples of a technique of calculating a line-of-sight angle include a technique of, by use of a reflected image (Purkinje image) of a near infrared light source on the cornea surface, calculating a line-of-sight angle from the distance between the center of the pupil and the Purkinje image, the technique being described in a literature (Takehiko Ohno, Naoki Mukawa, and Atsushi Yoshikawa, "Gaze tracking method based on an eyeball shape model," The Eighth Symposium on Sensing via Image Information, pp. 307 to 312, 2002) and a technique of, by use of a center of curvature of the cornea acquired from a Purkinje image, calculating a straight line connecting the center of curvature of the cornea to the center of the pupil as a line-of-sight angle.

When the difference between a face direction angle and a line-of-sight angle is equal to or greater than a predetermined value, the correction unit 14 in the processor 10 corrects a degree of eye opening calculated by the eye opening degree calculation unit 11 or corrects a threshold value which will be compared with the degree of eye opening.

When the difference between a face direction angle and a line-of-sight angle is large, a degree of eye opening is erroneously detected, and the degree of eye opening is recognized differently from the actual value. Examples of erroneous calculation of a degree of eye opening include two cases, one being a case of the degree of eye opening decreasing due to the upper eyelid falling according to the line-of-sight direction and the other being a case of the degree of eye opening increasing due to the upper eyelid rising according to the line-of-sight direction. The case of the degree of eye opening decreasing due to the eyelid falling according to the line-of-sight direction is a case of the face direction angle pointing upward or forward and the line-of-sight angle pointing downward. Further, the case of the degree of eye opening increasing due to the eyelid rising according to the line-of-sight direction is a case of the face direction angle pointing downward or forward and the line-of-sight angle pointing upward.

Figure 3:
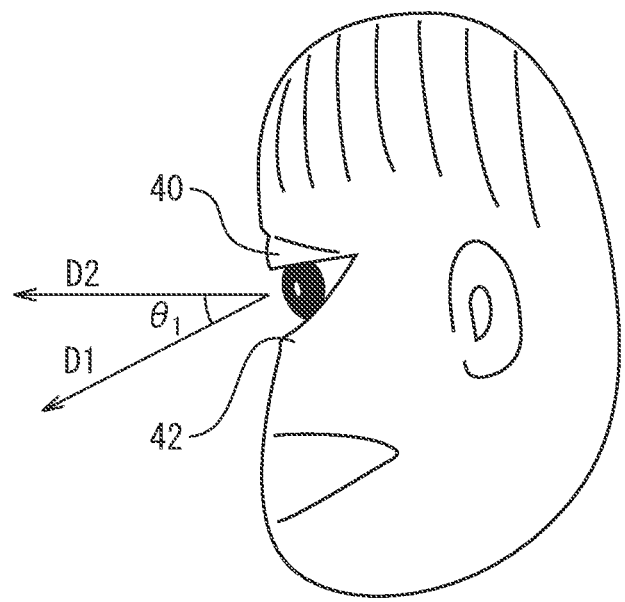
FIG. 3 is a schematic diagram illustrating a profile of a crew and illustrates a case of a face turned forward and a line of sight turned downward.

FIG. 3 is a schematic diagram illustrating the driver's profile and illustrates a case of the face turned forward and the line of sight turned downward. In FIG. 3, D1 denotes a line-of-sight direction, and D2 denotes a face direction. The angular difference between the D1 direction and the D2 direction is denoted by $\theta_1$. Further, assuming that a predetermined reference direction points to the front of the driver (horizontal direction) and a counterclockwise direction is a plus (+) direction in FIG. 3, a face direction angle is 0, and a line-of-sight angle is $-\theta_1$.

When the face direction angle points forward and the line-of-sight angle points downward as illustrated in FIG. 3, the distance between an upper eyelid 40 and a lower eyelid 42 is narrowed by a fall of the upper eyelid 40. Accordingly, a degree of eye opening in the case of the face direction angle pointing forward and the line-of-sight angle pointing downward is less than that in a case of both the face direction angle and the line-of-sight angle pointing forward. For a similar reason, a degree of eye opening in a case of the face direction angle pointing upward and the line-of-sight angle pointing downward is less than that in the case of both the face direction angle and the line-of-sight angle pointing forward.

When the driver's degree of arousal is determined based on a degree of eye opening, the degree of eye opening is compared with a predetermined determination threshold value (eye closure determination threshold value), and when the degree of eye opening is equal to or less than the determination threshold value, the degree of arousal is determined to be reduced. At this time, the determination threshold value is set on the assumption that the face direction angle and the line-of-sight angle point forward. In the case as illustrated in FIG. 3, the degree of eye opening is recognized less than the actual value, and therefore when a degree of arousal is determined based on the degree of eye opening, the degree of arousal may be erroneously determined to be reduced although the degree of arousal is originally not reduced.

Figure 4:
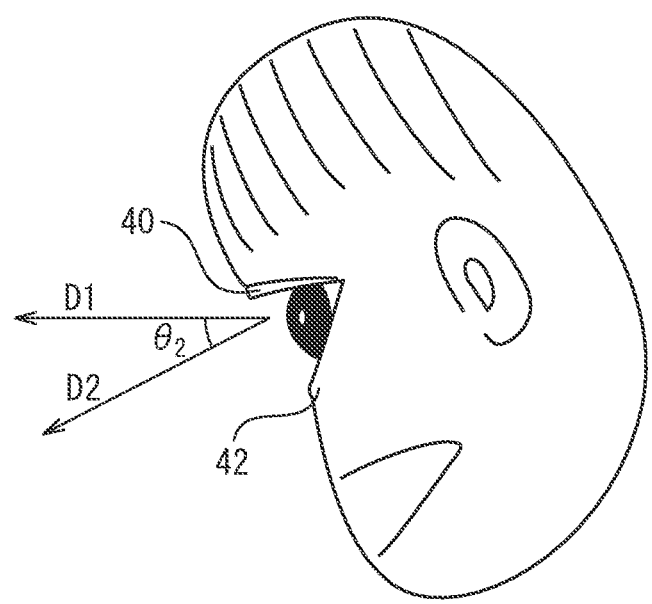
FIG. 4 is a diagram illustrating a case of the face turned downward and the line of sight turned forward.

Further, FIG. 4 is a diagram illustrating a case of the face turned downward and the line of sight turned forward. D1 denotes the line-of-sight direction, and D2 denotes the face direction also in FIG. 4. The angular difference between the D1 direction and the D2 direction is denoted by $\theta_2$. It is also assumed in FIG. 4 that the predetermined reference direction points to the front of the driver (horizontal direction) and the counterclockwise direction is a plus (+) direction of angles. In this case, the face direction angle is $-\theta_2$, and the line-of-sight angle is 0.

When the face direction angle points downward and the line-of-sight angle points forward as illustrated in FIG. 4, the distance between the upper eyelid 40 and the lower eyelid 42 is widened by a rise of the upper eyelid 40. Accordingly, a degree of eye opening in the case of the face direction angle pointing downward and the line-of-sight angle pointing forward is greater than that in the case of both the face direction angle and the line-of-sight angle pointing forward. For a similar reason, a degree of eye opening in a case of the face direction angle pointing downward and the line-of-sight angle pointing upward is greater than that in the case of both the face direction angle and the line-of-sight angle pointing forward. In such a case, a degree of eye opening is recognized greater than the actual value, and therefore when a degree of arousal is determined based on the degree of eye opening, the degree of arousal may be erroneously determined not to be reduced although the degree of arousal is originally reduced.

Accordingly, when the difference between a face direction angle and a line-of-sight angle is large, and the difference is equal to or greater than a predetermined value, the correction unit 14 in the processor 10 corrects a degree of eye opening calculated by the eye opening degree calculation unit 11. Further, when the difference between the face direction angle and the line-of-sight angle is large, and the difference is equal to or greater than the predetermined value, the correction unit 14 corrects a determination threshold value which will be compared with the degree of eye opening calculated by the eye opening degree calculation unit 11. Note that at least either one of a correction of a degree of eye opening and a correction of the determination threshold value is performed.

When the difference between the face direction angle and the line-of-sight angle is equal to or greater than the predetermined value, the correction unit 14 multiplies the degree of eye opening calculated by the eye opening degree calculation unit 11 by a correction factor A in accordance with equation (1) below and corrects the degree of eye opening to a value corresponding to the case of both the face and the line of sight pointing forward.

$$\text{degree of eye opening} \times A = \text{corrected degree of eye opening} \qquad (1)$$

For example, denoting the predetermined value by $\theta_{th}$ and the difference acquired by subtracting the line-of-sight angle from the face direction angle by $\theta$, the correction unit 14 calculates a corrected degree of eye opening from equation (1) when $|\theta| \geq \theta_{th}$ holds.

Further, when the difference between the face direction angle and the line-of-sight angle is equal to or greater than the predetermined value, the correction unit 14 corrects the determination threshold value which will be compared with the degree of eye opening in order to determine a degree of arousal. The correction unit 14 multiplies the determination threshold value by a correction factor B in accordance with equation (2) below and corrects the determination threshold value to a corrected determination threshold value corresponding to the current face direction angle and line-of-sight angle. Note that the determination threshold value before correction on the left side of equation (2) corresponds to a determination threshold value when both the face and the line of sight are turned forward.

$$\text{determination threshold value} \times B = \text{corrected determination threshold value} \qquad (2)$$

For example, denoting the predetermined value by $\theta_{th}$ and the difference acquired by subtracting the line-of-sight angle from the face direction angle by $\theta$, the correction unit 14 calculates a corrected determination threshold value from equation (2) when $|\theta| \geq \theta_{th}$ holds.

For example, $\theta_{th}$ is assumed to be 5 [deg]. Accordingly, when the absolute value of the difference $\theta$ is equal to or greater than 5 [deg], a correction of the degree of eye opening or the determination threshold value is performed, and when the absolute value of the difference $\theta$ is less than 5 [deg], a correction of the degree of eye opening or the determination threshold value is not performed.

The determination unit 15 in the processor 10 determines the driver's eye opening state, based on a corrected degree of eye opening, or a comparison result of the degree of eye opening with a corrected determination threshold value. For example, the determination unit 15 determines the driver's eye opening state by using a map associating a degree of eye opening with an eye opening state, the map being previously stored in the memory, and applying the map to the degree of eye opening. Further, when the comparison result of the degree of eye opening with the determination threshold value indicates that the degree of eye opening is equal to or less than the determination threshold value, the determination unit 15 determines that the eye opening state is degraded, and the degree of arousal is reduced.

When the driver's eye opening state is determined to be degraded or the driver's degree of arousal is determined to be reduced by the determination unit 15, the display 2 displays a warning to the driver in accordance with an instruction from the control device 100. Further, a warning by voice may be given along with a warning display on the display 2. Consequently, reduction in the driver's degree of arousal is suppressed.

Further, when the driver's eye opening state is determined to be degraded or the driver's degree of arousal is determined to be reduced by the determination unit 15, the vehicle control equipment 3 stops the vehicle at a safe place in accordance with an instruction from the control device 100. Consequently, dozing off at the wheel or the like that may occur due to reduction in the driver's degree of arousal is avoided in advance.

Figure 5:
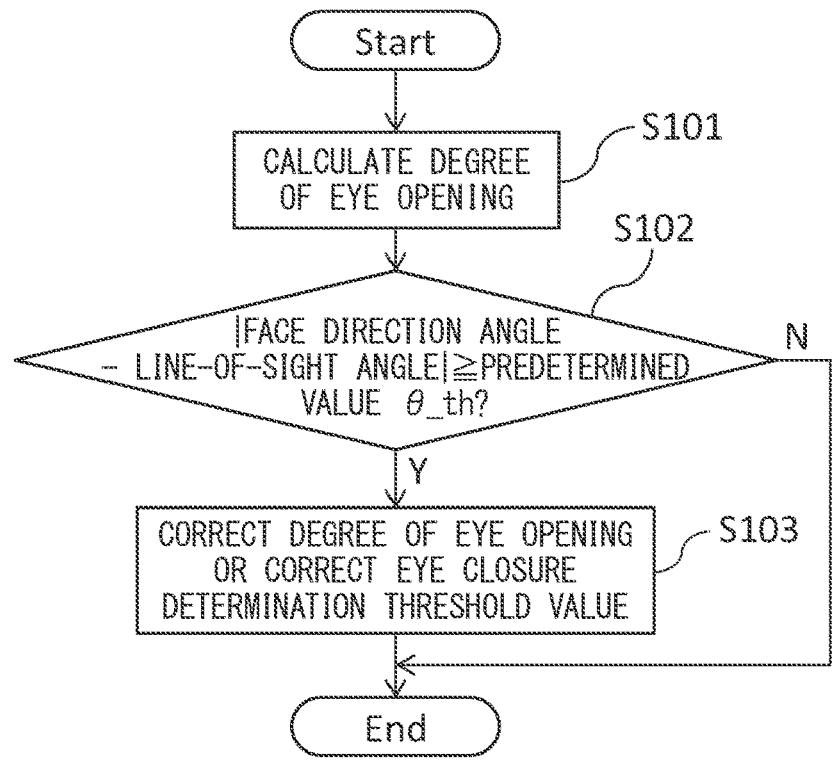
FIG. 5 is a flowchart illustrating processing performed by the processor in the control device at predetermined control intervals.

FIG. 5 is a flowchart illustrating processing performed by the processor 10 in the control device 100 at predetermined control intervals. First, the eye opening degree calculation unit 11 calculates the driver's degree of eye opening from an image generated by the driver monitoring camera 1 (step S101).

Next, the face direction angle calculation unit 12 calculates the driver's face direction angle with respect to the predetermined reference direction, and the line-of-sight angle calculation unit 13 calculates the driver's line-of-sight angle with respect to the predetermined reference direction. Then, whether the absolute value of the difference between the face direction angle and the line-of-sight angle is equal to or greater than the predetermined value $\theta_{th}$ is determined (step S102).

When the absolute value of the difference $\theta$ between the face direction angle and the line-of-sight angle is equal to or greater than the predetermined value $\theta_{th}$ in step S102, the processing advances to step S103. In step S103, the correction unit 14 corrects the degree of eye opening or corrects the determination threshold value.

On the other hand, when the absolute value of the difference $\theta$ is less than the predetermined value $\theta_{th}$ in step S102, the processing is ended without a correction of the degree of eye opening or a correction of the determination threshold value (End).

Next, a correction of a degree of eye opening performed by the correction unit 14 will be described in more detail. It is assumed that the correction unit 14 corrects a degree of eye opening when the difference $\theta$ is in a range of $-\theta_{max} \leq \theta \leq \theta_{max}$. For example, $\theta_{max} = 70$ [deg]. When the difference $\theta$ acquired by subtracting the line-of-sight angle from the face direction angle is less than $-\theta_{max}$, or the difference $\theta$ acquired by subtracting the line-of-sight angle from the face direction angle is greater than $\theta_{max}$, the correction unit 14 does not correct the degree of eye opening.

Specifically, when $\theta_{max} \geq \theta \geq \theta_{th}$ holds in the case of the face direction angle pointing upward or forward and the line-of-sight angle pointing downward ($\theta > 0$), the correction unit 14 calculates a corrected degree of eye opening from equation (1). Further, when $-\theta_{max} \leq \theta \leq \theta_{th}$ holds in the case of the face direction angle pointing downward or forward and the line-of-sight angle pointing upward ($\theta < 0$), the correction unit 14 calculates a corrected degree of eye opening from equation (1). When the conditions are not met, the correction unit 14 does not calculate a corrected degree of eye opening. Accordingly, when the conditions are not met, the degree of eye opening is not corrected.

Figure 6:
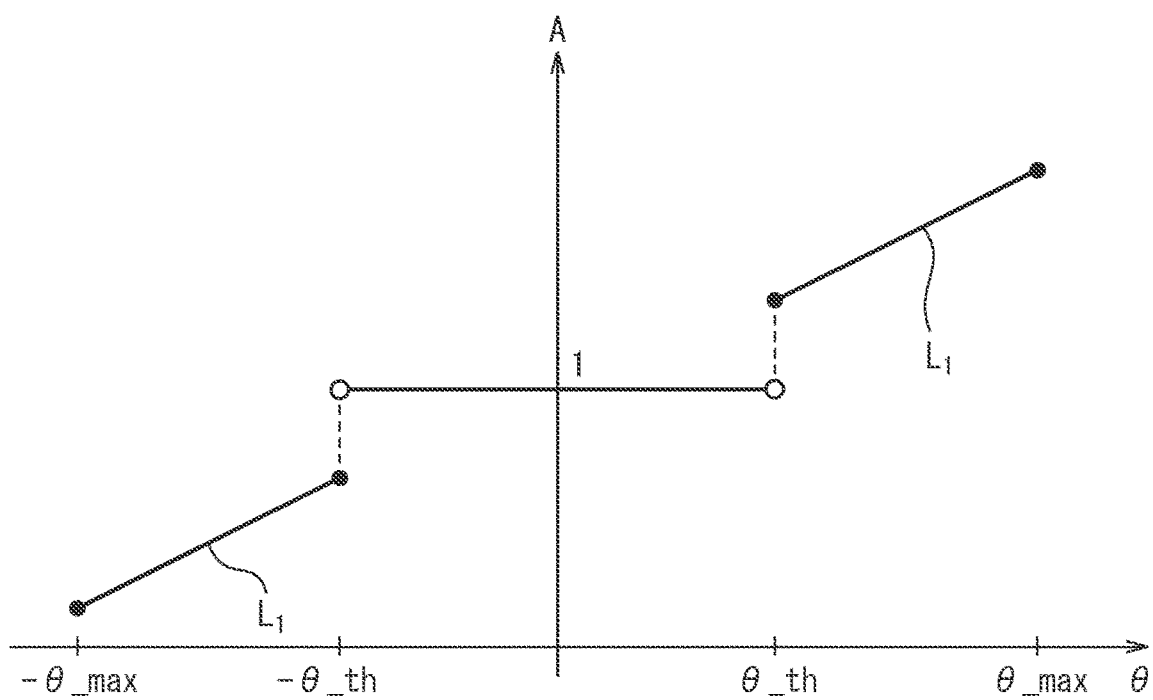
FIG. 6 is a diagram illustrating an example of a function defining a relation between a difference θ and a correction factor A.

The correction unit 14 approximates a relation between the difference $\theta$ between the face direction angle and the line-of-sight angle, and the correction factor A by a linear or nonlinear function and calculates a correction factor A according to a difference $\theta$ by use of the function. FIG. 6 is a diagram illustrating an example of a function defining a relation between the difference $\theta$ and the correction factor A. The correction factor A is calculated as follows, based on the function illustrated in FIG. 6. Note that, in the following description, Sa denotes a slope of a straight line $L_1$ in the function illustrated in FIG. 6, and for example, Sa=0.03.

when $-\theta_{max} \leq \theta \leq -\theta_{th}$,

A=Sa×θ+1 when $-\theta_{th} < \theta < \theta_{th}$,

A=1 when $\theta_{\_th} \leq \theta \leq \theta_{\_max}$,
A=Sa×θ+1

As described above, the correction unit 14 corrects a degree of eye opening when the absolute value of the difference θ is equal to or greater than $\theta_{\_th}$ and equal to or less than $\theta_{\_max}$. At this time, when the face direction angle points upward or forward and the line-of-sight angle points downward (θ>0), the correction unit 14 increases the value of the correction factor A as the difference θ increases. When the face direction angle points upward or forward and the line-of-sight angle points downward, the degree of eye opening decreases as the difference θ increases, and therefore by increasing the value of the correction factor A as the difference θ increases, the degree of eye opening is corrected to a value corresponding to the case of both the face and the line of sight pointing forward.

Further, when the face direction angle points downward or forward and the line-of-sight angle points upward (θ<0), the correction unit 14 decreases the value of the correction factor A as the difference θ decreases. When the face direction angle points downward or forward and the line-of-sight angle points upward, the degree of eye opening increases as the difference θ decreases, and therefore by decreasing the value of the correction factor A as the difference θ decreases, the degree of eye opening is corrected to the value corresponding to the case of both the face and the line of sight pointing forward.

Further, when the absolute value of the difference θ between the face direction angle and the line-of-sight angle is less than $\theta_{\_th}$, the correction unit 14 sets the correction factor A to "1." In this case, the difference θ between the face direction angle and the line-of-sight angle is small and the degree of eye opening is not erroneously calculated, and therefore the degree of eye opening is not corrected.

Further, the correction unit 14 also does not correct the degree of eye opening when the absolute value of the difference θ between the face direction angle and the line-of-sight angle exceeds $\theta_{\_max}$. In this case, the difference θ between the face direction angle and the line-of-sight angle is excessively large, and therefore the degree of eye opening is not corrected, and various types of processing based on the degree of eye opening are considered not performable. Accordingly, a determination of an eye opening state based on the degree of eye opening is also not made.

Next, a correction of a determination threshold value performed by the correction unit 14 will be described in more detail. When $\theta_{\_max} \geq \theta \geq \theta_{\_th}$ holds in the case of the face direction angle pointing upward or forward and the line-of-sight angle pointing downward (θ>0), the correction unit 14 calculates a corrected determination threshold value from equation (2) by a technique similar to a correction of a degree of eye opening. Further, when $-\theta_{\_max} \leq \theta \leq \theta_{\_th}$ holds in the case of the face direction angle pointing downward or forward and the line-of-sight angle pointing upward (θ<0), the correction unit 14 calculates a corrected determination threshold value from equation (2). When the conditions are not met, the correction unit 14 does not correct the determination threshold value.

Figure 7:
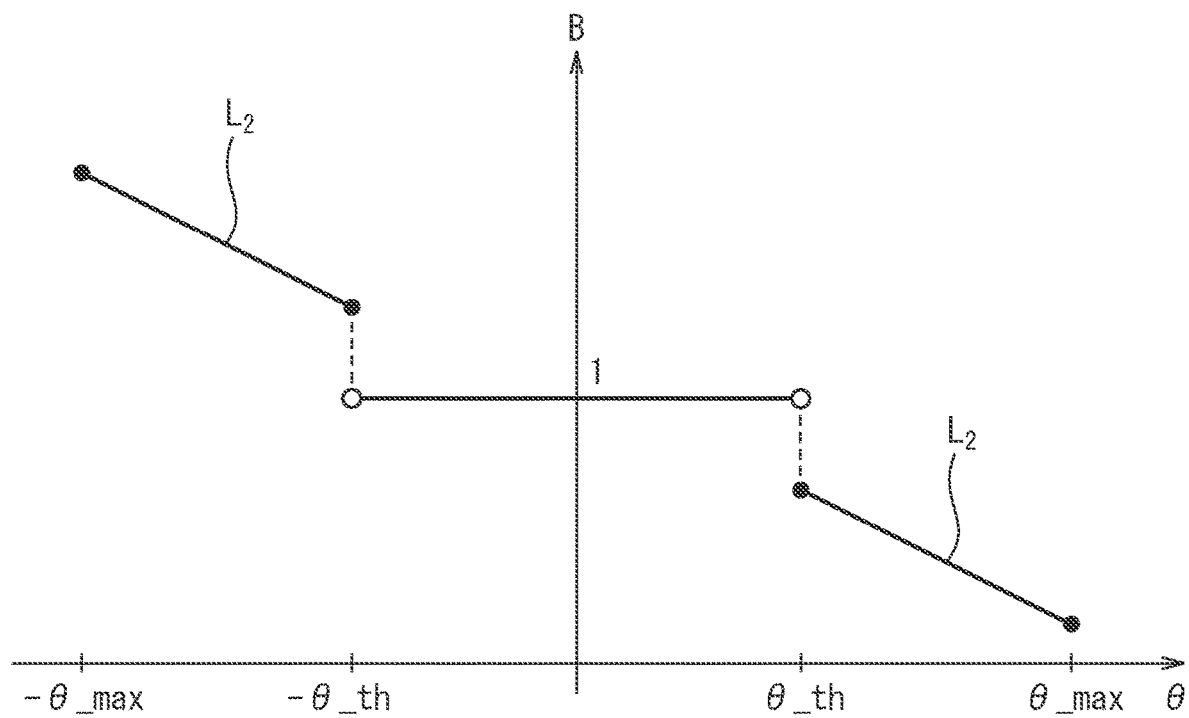
FIG. 7 is a diagram illustrating an example of a function defining a relation between a difference θ and a correction factor B.

Further, the correction unit 14 approximates a relation between the difference θ between the face direction angle and the line-of-sight angle, and the correction factor B by a linear or nonlinear function and calculates a correction factor B according to a difference θ by use of the function. FIG. 7 is a diagram illustrating an example of a function defining a relation between the difference θ and the correction factor B. The correction factor B is calculated as follows, based on the function illustrated in FIG. 7. Note that Sb denotes a slope of a straight line $L_2$ in the function illustrated in FIG. 7 in the following description, and for example, Sb=−0.03.

when $-\theta_{\_max} \leq \theta \leq \theta_{\_th}$,
B=Sb×θ+1
when $-\theta_{\_th} < \theta < \theta_{\_th}$,
B=1
when $\theta_{\_th} \leq \theta \leq \theta_{\_max}$,
B=Sb×θ+1

As described above, when the absolute value of the difference θ is equal to or greater than $\theta_{\_th}$ and equal to or less than $\theta_{\_max}$, the correction unit 14 corrects the determination threshold value. At this time, when the face direction angle points upward or forward and the line-of-sight angle points downward (θ>0), the correction unit 14 decreases the value of the correction factor B as the difference θ increases. When the face direction angle points upward or forward and the line-of-sight angle points downward, the degree of eye opening decreases as the difference θ increases, and therefore by decreasing the value of the correction factor B as the difference θ increases, a corrected determination threshold value decreases as the difference θ increases in accordance with equation (2). Accordingly, a degree of arousal is accurately determined based on the corrected determination threshold value corrected to a smaller value according to reduction in the degree of eye opening.

Further, when the face direction angle points downward or forward and the line-of-sight angle points upward (θ<0), the correction unit 14 increases the value of the correction factor B as the difference θ decreases. When the face direction angle points downward or forward and the line-of-sight angle points upward, the degree of eye opening increases as the difference θ decreases, and therefore by increasing the value of the correction factor B as the difference θ decreases, a corrected determination threshold value increases as the difference θ increases in accordance with equation (2). Accordingly, a degree of arousal is accurately determined based on the corrected determination threshold value corrected to a larger value according to increase in the degree of eye opening.

Further, when the absolute value of the difference θ between the face direction angle and the line-of-sight angle is less than $\theta_{\_th}$, the correction unit 14 sets the correction factor B to "1." In this case, the difference θ between the face direction angle and the line-of-sight angle is small and the degree of eye opening is not erroneously calculated, and therefore the determination threshold value is not corrected.

Further, the correction unit 14 also does not correct the determination threshold value when the absolute value of the difference θ between the face direction angle and the line-of-sight angle exceeds $\theta_{\_max}$. In this case, the difference θ between the face direction angle and the line-of-sight angle is excessively large, and therefore the determination threshold value is not corrected, and various types of processing based on the degree of eye opening are considered not performable. Accordingly, a determination of a degree of arousal by comparing the degree of eye opening with the determination threshold value is also not made.

Figure 8:
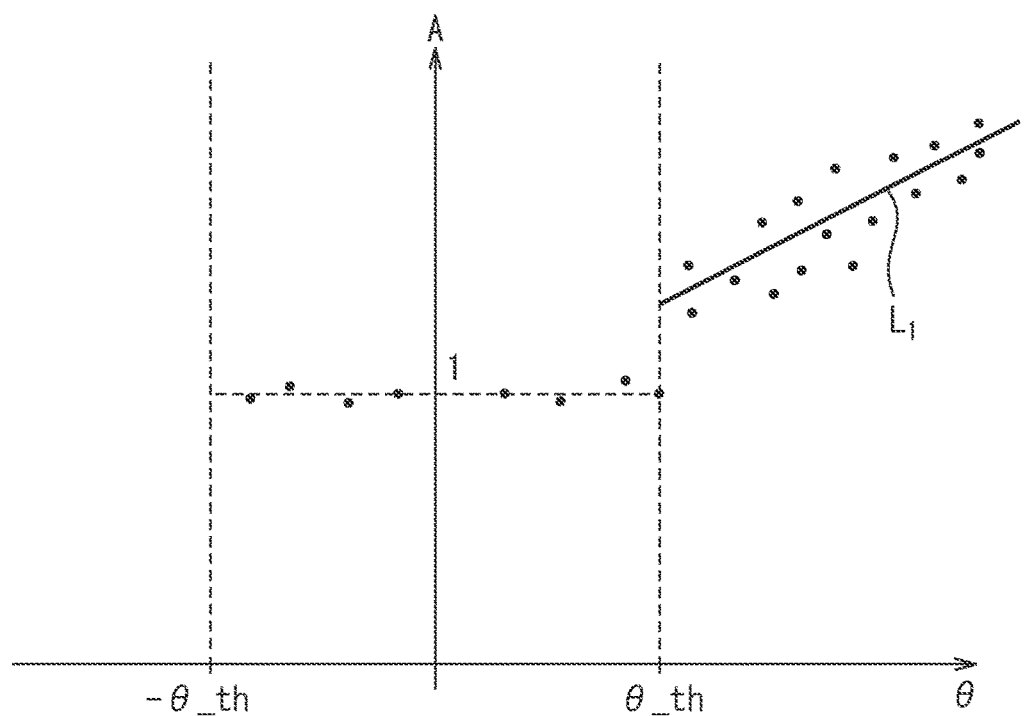
FIG. 8 is a diagram illustrating a technique of calculating a slope Sa of the correction factor A in a learning step.

For example, the slope Sa of the straight line $L_1$ illustrated in FIG. 6 is calculated by a learning step. FIG. 8 is a diagram illustrating a technique of calculating the slope Sa of the correction factor A in the learning step. The slope Sa is calculated within a time Ti from the processing start in the learning step. For example, Ti is set to around 10 [min].

In the learning step, the face direction angle is compared with a predetermined threshold value ωf, and the line-of-sight angle is compared with a predetermined threshold value ωg. Then, the mean value or the median of the degree of eye opening when the face direction angle <±ωf [deg] and the line-of-sight angle <±ωg [deg] hold is set to a reference value. By dividing the reference value by a degree of eye opening when at least either one of the face direction angle and the line-of-sight angle goes out of the range, a ratio Ac of the reference value to the degree of eye opening is calculated. For example, ωf=5 [deg] and ωg=5 [deg].

The thus calculated ratio Ac is a value corresponding to a correction factor A in the case of each of the absolute value of the face direction angle and the absolute value of the line-of-sight angle being equal to or greater than 5 [deg], and therefore by acquiring a plurality of samples of a pair of a ratio Ac and a relating difference θ, a function defining a relation between a ratio Ac and a difference θ (the straight line $L_1$ illustrated in FIG. 6) is determined.

FIG. 8 illustrates a state of plotting each point expressed by a ratio Ac and a difference θ relating to the ratio Ac on a coordinate system with the vertical axis representing the correction factor A and the horizontal axis representing the difference θ. The slope Sa of the straight line $L_1$ is calculated based on the ratio Ac and the difference θ by use of the least squares method or the like. As described above, when the slope Sa is determined, a correction factor A is determined according to the value of a difference θ. Note that while FIG. 8 illustrates a method of determining a slope Sa of a straight line $L_1$ in a region where θ>0 holds, the same holds for a region where θ<0 holds.

As described above, the correction unit 14 performs at least either one of a correction of a degree of eye opening and a correction of the determination threshold value. Switching between a correction of a degree of eye opening and a correction of the determination threshold value may be performed based on the time t elapsed from the processing start of eye opening degree calculation and the time Ti required for the learning step.

For example, denoting a processing start time of eye opening degree calculation by 0 and the current time by t, when t≤Ti holds, the correction unit 14 performs correction processing of the determination threshold value. Further, when t>Ti holds, the correction unit 14 performs correction processing of a degree of eye opening.

According to such processing, when t≤Ti holds, the aforementioned learning step is not completed, and therefore an eye opening state is determined by comparing a degree of eye opening with a corrected determination threshold value until the correction factor A is determined. Further, when t>Ti holds, the learning step is completed, and therefore a degree of eye opening is corrected using the correction factor A acquired by the learning by performing correction processing of the degree of eye opening, and an eye opening state is determined according to the corrected degree of eye opening.

While an example of the vehicle control system 200 being equipped on a vehicle and an eye opening state of a crew such as a driver being determined has been described in the description above, the present embodiment is not limited thereto. The present embodiment is widely applicable to a system determining an eye opening state of a human.

As described above, according to the present embodiment, a degree of eye opening or a determination threshold value which will be compared with the degree of eye opening is corrected according to the angular difference between a face direction angle and a line-of-sight angle, and therefore calculation precision of the degree of eye opening or the determination threshold value which will be compared with the degree of eye opening is improved. Accordingly, an eye opening state is precisely determined even when the face direction angle and the line-of-sight angle are different.

While preferred embodiments of the present invention have been described above, the present invention is not limited to the embodiments, and various modifications and changes can be made within the scope of the claims.

The invention claimed is:

1. An eye opening degree calculation device comprising:
a processor configured to:
calculate a degree of eye opening of a crew, based on an image in which a face of the crew appears;
calculate a face direction angle of the crew with respect to a predetermined reference direction, based on the image;
calculate a line-of-sight angle of the crew with respect to the predetermined reference direction, based on the image;
correct the degree of eye opening or a threshold value which is compared with the degree of eye opening, when a difference between the face direction angle and the line-of-sight angle is equal to or greater than a predetermined value; and
determine an eye opening state of the crew, based on the corrected degree of eye opening or a comparison result of the degree of eye opening with the corrected threshold value.

2. The eye opening degree calculation device according to claim 1, wherein the processor corrects the degree of eye opening to a value corresponding to a case of the face direction angle and the line-of-sight angle pointing forward, based on the difference.

3. The eye opening degree calculation device according to claim 1, wherein the processor corrects the degree of eye opening in such a way as to increase the degree of eye opening when the line-of-sight angle points more downward than the face direction angle and corrects the degree of eye opening in such a way as to decrease the degree of eye opening when the line-of-sight angle points more upward than the face direction angle.

4. The eye opening degree calculation device according to claim 3, wherein the processor increases an amount of correction of the degree of eye opening as the difference increases.

5. The eye opening degree calculation device according to claim 1, wherein the processor corrects the threshold value in such a way as to decrease the threshold value when the line-of-sight angle points more downward than the face direction angle and corrects the threshold value in such a way as to increase the threshold value when the line-of-sight angle points more upward than the face direction angle.

6. The eye opening degree calculation device according to claim 5, wherein the processor increases an amount of correction of the threshold value as the difference increases.

* * * * *